US011348664B1

(12) United States Patent
Kaneko et al.

(10) Patent No.: US 11,348,664 B1
(45) Date of Patent: May 31, 2022

(54) MACHINE LEARNING DRIVEN CHEMICAL COMPOUND REPLACEMENT TECHNOLOGY

(71) Applicant: NotCo Delaware, LLC, Santiago (CL)

(72) Inventors: Kyohei Kaneko, Oakland, CA (US); Nathan O'Hara, Westwood, MA (US); Isadora Nun, San Francisco, CA (US); Aadit Patel, Burlingame, CA (US); Kavitakumari Solanki, San Bruno, CA (US); Karim Pichara, San Francisco, CA (US)

(73) Assignee: NotCo Delaware, LLC, Santiago (CL)

( * ) Notice: Subject to any disclaimer, the term of this patent is extended or adjusted under 35 U.S.C. 154(b) by 0 days.

(21) Appl. No.: 17/351,069

(22) Filed: Jun. 17, 2021

(51) Int. Cl.
*G01N 33/48* (2006.01)
*G01N 33/50* (2006.01)
*G16C 20/70* (2019.01)
*G16C 20/20* (2019.01)
*G06N 3/08* (2006.01)
*G16C 20/40* (2019.01)
(Continued)

(52) U.S. Cl.
CPC .............. *G16C 20/70* (2019.02); *G06N 3/04* (2013.01); *G06N 3/08* (2013.01); *G16B 40/00* (2019.02); *G16B 99/00* (2019.02); *G16C 20/20* (2019.02); *G16C 20/40* (2019.02); *G16C 20/50* (2019.02)

(58) Field of Classification Search
CPC ........ G16C 20/70; G16C 20/20; G16C 20/40; G16C 20/50; G06N 3/04; G06N 3/08; G16B 40/00; G16B 99/00
See application file for complete search history.

(56) References Cited

U.S. PATENT DOCUMENTS 8,419,433 B2    4/2013    Do et al.
8,647,121 B1    2/2014    Witlin et al.
(Continued)

FOREIGN PATENT DOCUMENTS

WO    2004083451 A1    9/2004
WO    2013052824 A1    4/2013
(Continued)

OTHER PUBLICATIONS

Cromwell et al. Computational creativity in the culinary arts. Proceedings of the Twenty-Eighth International Florida Artificial Intelligence Research Society Conference, pp. 38-42. (Year: 2015).*
(Continued)

*Primary Examiner* — Russell S Negin
(74) *Attorney, Agent, or Firm* — Haverstock & Owens, A Law Corporation

(57) ABSTRACT

Techniques to suggest alternative chemical compounds that can be used to recreate or mimic a target flavor using artificial intelligence are disclosed. A neural network based model is trained on source chemical compounds and their corresponding flavors and odors. The neural network-based model learns compound embeddings of the source chemical compounds and a target chemical compound of a food item. From the compound embeddings, one or more chemical compounds that are closest to the target chemical compound may be determined by a distance metric. Each suggested chemical compound is an alternative that can be used to recreate functional features of the target chemical compound.

20 Claims, 6 Drawing Sheets

(51) Int. Cl.
  *G06N 3/04* (2006.01)
  *G16C 20/50* (2019.01)
  *G16B 40/00* (2019.01)
  *G16B 99/00* (2019.01)

(56) References Cited

U.S. PATENT DOCUMENTS

| | | | |
|---|---|---|---|
| 8,775,341 | B1 | 7/2014 | Commons |
| 9,519,620 | B1 | 12/2016 | Pinel et al. |
| 10,325,181 | B2 | 6/2019 | Xu et al. |
| 10,515,715 | B1 | 12/2019 | Pappas et al. |
| 10,915,818 | B1 | 2/2021 | Patel et al. |
| 10,957,424 | B1 | 3/2021 | Navon et al. |
| 10,962,473 | B1 | 3/2021 | O'Hara et al. |
| 10,970,621 | B1 | 4/2021 | Pichara et al. |
| 10,984,145 | B1 | 4/2021 | Hutchinson et al. |
| 10,993,465 | B2 | 5/2021 | Pichara et al. |
| 11,164,069 | B1 | 11/2021 | Korsunsky et al. |
| 11,164,478 | B2 | 11/2021 | Pichara et al. |
| 2002/0184167 | A1 | 12/2002 | McClanahan |
| 2003/0157725 | A1 | 8/2003 | Franzen et al. |
| 2007/0139667 | A1 | 6/2007 | Russell et al. |
| 2009/0055247 | A1 | 2/2009 | Jackson |
| 2013/0149679 | A1 | 6/2013 | Tokuda et al. |
| 2013/0222406 | A1 | 8/2013 | Wolfe et al. |
| 2016/0110584 | A1 | 4/2016 | Remiszewski et al. |
| 2016/0358043 | A1 | 12/2016 | Mu et al. |
| 2017/0116517 | A1 | 4/2017 | Chee et al. |
| 2017/0139902 | A1 | 5/2017 | Byron et al. |
| 2017/0238590 | A1 | 8/2017 | Bansal-Mutalik et al. |
| 2017/0345185 | A1 | 11/2017 | Byron et al. |
| 2018/0101784 | A1 | 4/2018 | Rolfe et al. |
| 2018/0192680 | A1 | 7/2018 | Fraser et al. |
| 2018/0203921 | A1 | 7/2018 | Privault et al. |
| 2018/0293489 | A1 | 10/2018 | Eyster et al. |
| 2019/0171707 | A1 | 6/2019 | Rapaport |
| 2019/0200797 | A1 | 7/2019 | Diao et al. |
| 2019/0228855 | A1 | 7/2019 | Leifer et al. |
| 2019/0228856 | A1 | 7/2019 | Leifer et al. |
| 2019/0295440 | A1 | 9/2019 | Hadad |
| 2020/0268032 | A1* | 8/2020 | Okuyama ............... A23L 27/82 |
| 2020/0309746 | A1 | 10/2020 | Sakai |
| 2020/0365053 | A1 | 11/2020 | Pichara et al. |

FOREIGN PATENT DOCUMENTS

| | | |
|---|---|---|
| WO | 2016010097 A1 | 1/2016 |
| WO | 2017070605 A1 | 4/2017 |
| WO | 2020237214 A1 | 11/2020 |
| WO | 2021026083 A1 | 2/2021 |
| WO | 2021071756 A1 | 4/2021 |

OTHER PUBLICATIONS

Park et al. FlavorGraph: a large-scale food-chemical graph for generating food representations and recommending food pairings. Scientific Reports: Nature Research. vol. 11. Jan. 13, 2021, 13 pages.*

Patel, U.S. Appl. No. 16/9240,006, filed Jul. 8, 2020, Office Action, dated Sep. 9, 2020.

Patel, U.S. Appl. No. 16/9240,006, filed Jul. 8, 2020, Notice of Allowance, dated Dec. 2, 2020.

Navon, U.S. Appl. No. 16/989,413, filed Aug. 10, 2020, Office Action, dated Sep. 30, 2020.

Navon, U.S. Appl. No. 16/989,413, filed Aug. 10, 2020, Notice of Allownace, dated Jan. 6, 2021.

Korsunsky, U.S. Appl. No. 17/167,981, filed Feb. 4, 2021, Office Action, dated Apr. 15, 2021.

Zou et al., "Regularization and Variable Selection via the Elastic Net", Department of Statistics, Stanford University, dated Dec. 5, 2003, 29 pages.

Bowman et al., "Generating Sentences from a Continuous Space", May 2016.

Rudinger et al., Skip-Prop: Representing Sentences with One Vector Pre Proposition, 12th International Conference or Computational Semantics, dated 2017, 7 pages.

Karamanolakis et al., "Item Recommendation with Variational Autoencoders and Heterogeneous Priors", DLRS, dated Oct. 2018, 5 pages.

Eating bird food, "Vegan "Chicken" Salad", https://www.eatingbirdfood.com/simple-vegan-mock-chicken-salad/, Apr. 5, 2017, downloaded Mar. 11, 2021. (Year: 2017).

Rong, Xin. word2vec Parameter Learning Explained. arXiv:1411.2738v4 [cs.CL] Jun. 5, 2016. (Year: 2016).

Salvador, Amaia, et al. "Learning cross-modal embeddings for cooking recipes and food images." Proceedings of the EEE conference on computer vision and pattern recognition. 2017. (Year: 2017).

David Xu, "Machine Learning for Flavor Development," Bachelor's Thesis, Harvard College, School of Engineering and Applied Sciences, Apr. 5, 2019, 69 pages.

Hattab et al., Application of an Inverse Neural Network Model for the Identification of Optimal Amendment to Reduce Copper Toxicity in Phytoremediated Contaminated Soils, Journal of Geochemical Exploration, Elsevier, 2014, 136, pp. 14-23, 2014. (Year: 2014).

Kieaibi E., Determination of Protein Secondary Structure from Infrared Spectra Using Partial Least-Squares Regression, 9 pages, 2016 (Year: 2016).

Yang et al., "Obtaining information about protein secondary structures in aqueous solution using Fourier transform IR spectroscopy", Published online Feb. 5, 2015, nature protocols, 16 pages.

XGBoost, "Python Package Introduction", https://xgboost.readthedocs.io/en/latest/python/python_intro.html, last viewed on Nov. 5, 2020, 5 pages.

GitHub.com, "CMBI/DSSP", https://github.com/cmbi/dssp, last viewed on Nov. 5, 2020. 4 pages.

Wilcox et al., "Determination of Protein Secondary Structure from Infrared Spectra Using Partial Least-Squares Regression", dated 2016 American Chemical Society, 9 pages.

Sigma-Aldrich, "IR Spectrum Table and Chart", https://www.sigmaaldrich.com/technical-documents/articles/biology/ir-spectrum-table.html, last viewed on Nov. 5, 2020, 6 pages.

SciPy.org, "scipy.signal.savgol_filter", https://docs.scipy.org/doc/scipy/reference/generated/scipy.signal.savgol_filter.html, last viewed on Nov. 5, 2020, 3 pages.

SciPy.org, "scipy.integrate.simps", https://docs.scipy.org/doc/scipy/reference/generated/scipy.integrate.simps.html, last viewed on Nov. 5, 2020, 2 pages.

Scikitlearn.org, "sklearn.neighbors.KNeighborsRegressor", https://scikit-learn.org/stable/modules/generated/sklearn.neighbors.KNeighborsRegressor.html, last viewed on Nov. 5, 2020, 5 pages.

Scikitlearn.org, "sklearn.model_selection.GridSearchCV", https://scikit-learn.org/stable/modules/generated/sklearn.model_selection.GridSearchCV.html, last viewed on Nov. 5, 2020, 7 pages.

Scikitlearn.org, "sklearn.linear_model.lasso", https://scikit-learn.org/stable/modules/generated/sklearn.linear_model.Lasso.html, last viewed on Nov. 5, 2020, 6 pages.

Scikitlearn.org, "sklearn.cross_decomposition.PLSRegression", https://scikit-learn.org/stable/modules/generated/sklearn.cross_decomposition.PLSRegression.html , last viewed on Nov. 5, 2020, 5 pages.

Scikitlearn.org, "3.2.4.1.3. sklearn.linear_model.LassoCV", https://scikit-learn.org/stable/modules/generated/sklearn.linear_model.LassoCV.html, last viewed on Nov. 5, 2020, 6 pages.

ProDry, "DSSP Tools", http://prody.csb.pitt.edu/manual/reference/proteins/dssp.html, last viewed on Nov. 5, 2020, 2 pages.

Cao et al.,"Optimization of Formulations Using Robotic Experiments Driven by Machine Learning DoE", Cell Reports Physical Science, Jan. 20, 2021, 17 pages.

The International Searching Authority, "Search Report" in application No. PCT/US2021/015328, dated. Mar. 18, 2021, 13 pages .

The International Searching Authority, "Search Report" in application No. PCT/US2020/043330, dated Sep. 16, 2020, 16 pages.

(56) References Cited

OTHER PUBLICATIONS

Rudinger et al., Skip-Prop: Representing Sentences with One Vector Pre Proposition, 12th International Conference on Computational Semantics, dated 2017, 7 pages.
Nour Hattab et al., "Application of an inverse neural network model for the identification of optimal amendment to reduce Copper toxicity in phytoremediated contaminated soils," 2014, 40 pages.
International Searching Authority, "Search Report," in application No. PCT/US2021/017111, dated Apr. 23, 2021, 29 pages.
Current Claims in application No. PCT/US2021/017111, dated Apr. 23, 2021, 6 pages.
Current Claims in application No. PCT/US2021/015328, dated Mar. 18, 2021, 4 pages,.
Current Claims in application No. PCT/US2020/043330, dated Sep. 2020, 5 pages.
Bowman et al., "Generating Sentences from a Continuous Space", dated May 12, 2016, 12 pages.
Yuan et al., "An Inductive Content-Augmented Network Embedding Model for Edge Artificial Intelligence", IEEE Transaction on Industrial Informatics, vol. 15 No. 7, Jul. 2019, pp. 4295-4305.
Hodgkin, "The Castlemaine Project: Development of an AI-based Drug Design Support System", Molecular Modelling and Drug Design, 1994, pp. 137-169.
Peiretti et al., "Artificial Intelligence: The Future for Organic Chemistry?", ACS Omega, 2018, 3 (10), pp. 13263-13266.
Fromm et al., "A Vector Space model for Neural Network Functions: Inspirations from Similarities between the Theory of Connectivity and the Logarithmic Time Course of Word Production", Frontiers in Systems Neuroscience, Aug. 28, 2020, 10 pages.

\* cited by examiner

MACHINE LEARNING DRIVEN CHEMICAL COMPOUND REPLACEMENT TECHNOLOGY

TECHNICAL FIELD

One technical field of the present disclosure is artificial intelligence and machine learning, as applied to food. Another technical field is food science. The disclosure relates, in particular, to use of machine learning to suggest alternative chemical compounds that can be used to recreate functional properties of chemical compounds that are present in products, such as food items.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Today, many negative consequences of use of animals in the food industry are known, such as deforestation, pollution, human health conditions, and allergies, among others. In contrast, a plant-based diet is associated with improved health and well-being and reduces risk of diseases. Not only is a plant-based diet only good for human health but it is also good for the Earth's health. Research has shown that production of plant-based food items generates less greenhouse emissions and require less energy, water, and land than production of animal-based food items. There are plant alternatives to animal-based food items. For example, plant alternatives to meat include veggie burgers and other vegan meat food items. However, these alternatives do not match the taste and texture of meat.

Accordingly, there is a need for improved techniques to mimic a food item, such as an animal-based food item, by matching sensory attributes as much as possible. Unfortunately, many techniques for development of new foods rely upon time-consuming, inaccurate, manual laboratory work in which different ingredients are combined in different ways and tested. These approaches are inefficient, involve extensive time to develop a single successful food formula, and waste physical resources.

SUMMARY

The appended claims may serve as a summary of the invention.

BRIEF DESCRIPTION OF THE FIGURES

The present invention is illustrated by way of example, and not by way of limitation, in the figures of the accompanying drawings and in which like reference numerals refer to similar elements and in which.

DETAILED DESCRIPTION

Figure 1:
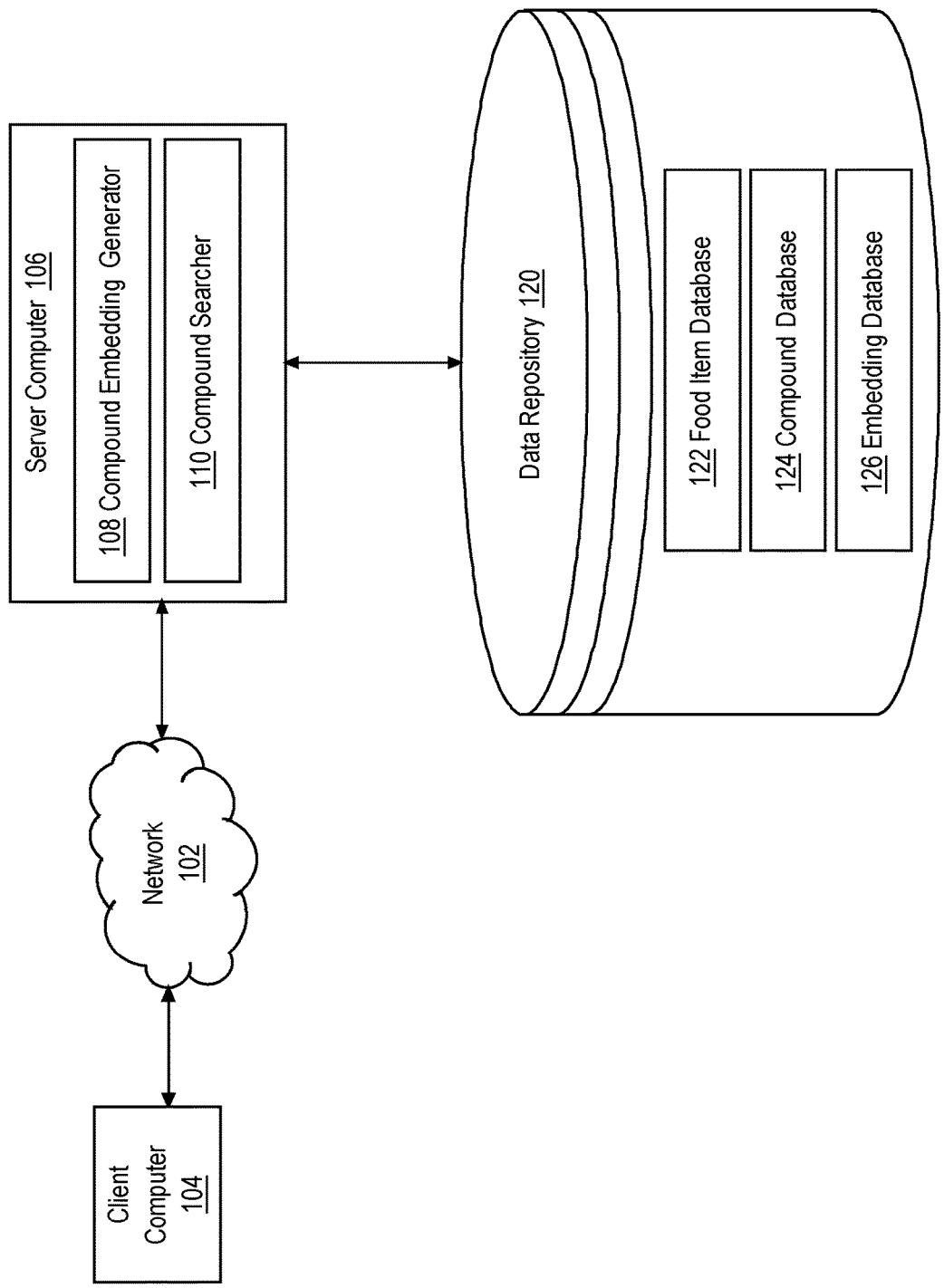
FIG. 1 illustrates an example networked computer system with which various embodiments may be practiced.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

Embodiments are described herein in sections according to the following outline:
    1.0 GENERAL OVERVIEW
    2.0 STRUCTURAL OVERVIEW
    3.0 FUNCTIONAL OVERVIEW
        3.1 COMPOUND EMBEDDING GENERATOR
            3.1.1 GRAPH NEURAL NETWORK
            3.1.2 FEED FORWARD NETWORK
            3.1.3 COMPOUND EMBEDDINGS
        3.2 COMPOUND SEARCHER
    4.0 EXAMPLE SEARCH FLOW
    5.0 PROCEDURAL OVERVIEW
    6.0 HARDWARE OVERVIEW
    7.0 SOFTWARE OVERVIEW
    8.0 OTHER ASPECTS OF DISCLOSURE

1.0 General Overview

Computer-implemented techniques for generating alternative chemical compounds that can be used to recreate or mimic flavors of target chemical compounds using artificial intelligence are disclosed.

In some embodiments, a neural network based model is trained on source chemical compounds and their corresponding flavors and odors. The trained neural network based model generates source compound embeddings of the source chemical compounds. The trained neural network based model generates a target compound embedding of a target chemical compound that is present in a food item. From the source compound embeddings, one or more alternative chemical compounds of the source chemical compounds that are closest to the target chemical compound, based on a distance metric, may be determined. Each alternative chemical compound may be used to recreate the flavor of the target chemical compound.

In an embodiment, a computer-implemented method of suggesting chemical compounds as substitutes for a chemical compound that is present in a food item, comprising: training an artificial intelligence model based on first digital data representing plurality of source chemical compounds and second digital data representing flavors and odors of the plurality of source chemical compounds; applying the trained artificial intelligence model to the plurality of source chemical compounds to generate a plurality of source compound embeddings for the plurality of source chemical compounds; applying the trained artificial intelligence model to a target chemical compound to generate a target compound embedding for the target chemical compound, the target chemical compound is a chemical compound that is present in a particular food item; determining, from the plurality of source chemical compounds, one or more alternative chemical compounds for which corresponding source compounding embeddings are closest to the target compound embedding for the target chemical compound.

All embodiments disclosed and claimed herein are directed to a computer-implemented programmed processes that interact with digital data to provide a practical application of computing technology to the problem of generating alternative chemical compounds that can be used to recreate functional (e.g., sensorial) properties, such as flavor, texture, etc., of target chemical compounds that may be expensive or can only be found from an animal source. The disclosure is not intended to encompass techniques for organizing human activity, for performing mental processes, or for performing a mathematical concept, and any interpretation of the claims to encompass such techniques would be unreasonable based upon the disclosure as a whole.

Other embodiments, aspects, and features will become apparent from the reminder of the disclosure as a whole.

2.0 Structural Overview

FIG. 1 illustrates an example networked computer system 100 with which various embodiments may be practiced. FIG. 1 is shown in simplified, schematic format for purposes of illustrating a clear example and other embodiments may include more, fewer, or different elements. FIG. 1, and the other drawing figures and all of the description and claims in this disclosure, are intended to present, disclose, and claim a technical system and technical methods comprising specially programmed computers, using a special-purpose distributed computer system design and instructions that are programmed to execute the functions that are described. These elements execute functions that have not been available before to provide a practical application of computing technology to the problem of generating alternative chemical compounds that can be used to recreate functional (e.g., sensorial) properties, such as flavor, texture, etc., of target chemical compounds in food items. In this manner, the disclosure presents a technical solution to a technical problem, and any interpretation of the disclosure or claims to cover any judicial exception to patent eligibility, such as an abstract idea, mental process, method of organizing human activity or mathematical algorithm, has no support in this disclosure and is erroneous.

In the example FIG. 1, the networked computer system 100 comprises a client computer(s) 104, a server computer 106, a data repository(ies) 120, which are communicatively coupled directly or indirectly via one or more networks 102. In an embodiment, the server computer 106 broadly represents one or more computers, such as one or more desktop computers, server computers, a server farm, a cloud computing platform (like AMAZON EC2® cloud computing platform, GOOGLE CLOUD® cloud computing platform, container orchestration (KUBERNETES® container orchestration, DOCKER® container orchestration, etc.)), or a parallel computer, virtual computing instances in public or private datacenters, and/or instances of a server-based application.

The server computer 106 includes one or more computer programs or sequences of program instructions that is organized to implement compound embedding generating functions and compound searching functions. Programs or sequences of instructions organized to implement the compound embedding generating functions may be referred to herein as a compound embedding generator 108. Programs or sequences of instructions organized to implement the compound generating functions may be referred to herein as a compound searcher 110.

In an embodiment, the compound embedding generator 108 is programmed to generate a compound embedding for a chemical compound. A compound embedding is an encoded representation of a chemical compound and provides information regarding similarities between the structure of the chemical compound and odors and flavors of the chemical compound. As further discussed below, the compound embedding generator 108 may be applied to each source chemical compound from a source compound database and to any of the chemical compounds present in a food item.

In an embodiment, the compound searcher 110 is programmed to suggest (determine, generate, predict) one or more alternative chemical compounds for a food item based on a particular chemical compound present in the food item that has been selected for replacement. Each alternative chemical compound recreates functional properties, such as flavor, smell, texture, etc., of that particular chemical compound.

In some embodiments, to provide modularity and separation of function, the compound embedding generator 108 and the compound searcher 110 are implemented as a logically separate program, process or library.

The server computer 106 also includes receiving instructions (not illustrated) and displaying instructions (not illustrated). The receiving instructions are programmed to receive data from a client computer 104 and/or a data repository 120 for further processing. For example, the receiving instructions may be programmed for receiving user input, such as user input specifying food items, chemical compounds, a number of suggested alternative compounds to be generated, etc. The displaying instructions are programmed to cause one or more computing devices, such as a client computer 104 to display a graphical user interface (GUI) including content, such as content from data repository 120 and/or generated by the compound embedding generator 108 and the compound searcher 110. Other sets of instructions may be included to form a complete system such as an operating system, utility libraries, a presentation layer, database interface layer and so forth.

Computer executable instructions described herein may be in machine executable code in the instruction set of a CPU and may have been compiled based upon source code written in Python, JAVA, C, C++, OBJECTIVE-C, or any other human-readable programming language or environment, alone or in combination with scripts in JAVASCRIPT, other scripting languages and other programming source text. In another embodiment, the programmed instructions also may represent one or more files or projects of source code that are digitally stored in a mass storage device such as non-volatile RAM or disk storage, in the systems of FIG. 1 or a separate repository system, which when compiled or interpreted cause generating executable instructions which when executed cause the computer to perform the functions or operations that are described herein with reference to those instructions. In other words, the figure may represent the manner in which programmers or software developers organize and arrange source code for later compilation into an executable, or interpretation into bytecode or the equivalent, for execution by the server computer 106.

The server computer 106 may be coupled to the data repository 120 that includes a food item database 122, a source compound database 124, and an embedding database 126. As used herein, the term "database" refers to a corpus of data, organized or unorganized, in any format, with or without a particular interface for accessing the corpus of data. Each database 122, 124, 126 may be implemented using memory, e.g., RAM, EEPROM, flash memory, hard disk drives, optical disc drives, solid state memory, or any type of memory suitable for database storage.

The food item database 122 includes a plurality of food items and information about the plurality of food item. A food item in the food item database 122 may be plant-based or animal-based. An example plant-based food item is tofu. An example animal-based food item is pulled pork.

Each food item in the food item database 122 is associated with gas chromatography mass spectrometry (GCMS) data obtained using GCMS techniques. GCMS techniques may be used to perform a GCMS analysis on a food item to determine the molecular composition of a food item. GCMS data may include one or more readouts, with each of the one or more readouts including a list of chemical compounds of the food item. For example, a first readout may include a human-verified list of chemical compounds, and a second readout may include a software-produced list of chemical compounds.

In an embodiment, the human-verified list of chemical compounds for the food item may include compound data, odor threshold data, and concentration data. The human-verified list of chemical compounds may stem from a predetermined list of chemical compounds with known odor thresholds. An odor threshold represents the lowest concentration of a chemical compound required for a human to be able to detect it within a solution, such as water with parts per billion as the unit. (It is noted that odors are relevant when creating a flavor. Studies suggest that odor is the dominant role in our experience of food.) A lab technician may check the existence of each chemical compound from the predetermined list by analyzing the retention time of the compound and the presence of its ions within the corresponding GCMS spectrum, and may determine the concentration of each of those chemical compounds in the food item by comparing it with the spectrum of an added baseline sample.

In an embodiment, the software-produced list of chemical compounds for the food item may include compound data, concentration data, and confidence data. The compound data and concentration data in the software-produced list are similarly configured as the compound data and concentration data in the human-verified list, in that the compound data includes chemical compounds that are present in the food item and the concentration data includes the concentration of each of those chemical compounds that are present in the food item. The confidence data in the software-produced list includes a score for each chemical compound indicating the likelihood of that chemical compound being present in the food item. The chemical compounds are automatically found by a GCMS software.

The readouts from the GCMS analysis are combined into a compound list for the food item, with chemical compounds from the first readout (e.g., human-verified list of compounds) weighted higher than chemical compounds from the second readout (e.g., software produced list of compounds) as odor thresholds of the chemical compounds from the second readout may be unknown and/or the confidence may be lower. The compound list also includes the concentration of each of the chemical compounds in the list.

In an embodiment, the compound list is presented, for example, in a GUI, to a user to select therefrom a target chemical compound for replacement. In an embodiment, each chemical compound in the list may be ranked by its ratio between odor threshold and concentration of that chemical compound. As such, since the second readout is not associated with odor thresholds, and as such the importance of each chemical compound from the second readout is unknown, chemical compounds from the second readout are ranked lower than chemical compounds from the first readout and are at the end of the combined compound list.

Each chemical compound in the combined compound list may be associated with a simplified molecular-input line-entry system (SMILES) based notation describing its corresponding structure, although other suitable notations that allow for chemical information processing are also contemplated. For example, the compound structure of vanillin may be represented as O=Cc1ccc(O)c(OC)c1COc1cc(C=O)ccc1O.

The combined compound list associated with each food item is stored in the food item database 122.

The source compound database 124 includes a plurality of source chemical compounds and information about the plurality of source chemical compounds, including structural and organoleptic information. The source compound database 124 also includes associations between the plurality of source chemical compounds and ingredients that contain them. In an embodiment, the ingredients associated with the plurality of source chemical compounds are natural ingredients. Associations with natural ingredients are useful for multiple reasons. First, using natural ingredients rather than flavorings are preferable for consumer transparency and provides potential for novel ingredient combinations. Secondly, compounds used in flavorings must be able to be extracted from natural ingredients to be considered a "Natural Flavor." Therefore, associations with natural ingredients can help flavorists select potential natural sources from which to extract flavorings. In an embodiment, the ingredients associated with the plurality of source chemical compounds are plant-based ingredients.

In an embodiment, data in the source compound database 124 may be obtained from different sources of knowledge, including open source databases such as the FlavorDB database, the FooDB database, the Good Scents Company database, or the like. Table 1 shows example information associated with each source chemical compound stored in the source compound database 124.

TABLE 1

| Compound Information | Description |
|---|---|
| Properties | Structural information, class, category |
| Databases | Database identifier in various databases (web sources) |
| Synonyms | Set of synonyms |
| Flavors | Tags, descriptions, type |
| Odors | Tags, descriptions, type, strength, substantivity |
| Ingredients | Natural ingredients the compound is found in |

The source chemical compound may be compounds certified by the Flavor & Extract Manufacturers Association (FEMA) and, as such, may be used by flavor houses to recreate flavors, as these source chemical compounds are certified GRAS (generally regarded as safe). Each source chemical compound in the source compound database 124 may be associated with a SMILES based notation describing its corresponding structure, although other suitable notations that allow for chemical information processing are also contemplated. A training dataset, for training the compound embedding generator 108, includes compound structures and corresponding flavor tags and/or odor tags of at least a subset of the source chemical compounds from the source compound database 124.

In an embodiment, the embedding database 126 includes compound embeddings generated by the compound embedding generator 108. The compound embeddings include source compound embeddings that correspond with source chemical compounds in the training dataset. The source compound embeddings that correspond with the source chemical compounds in the training dataset are used by the compound searcher 110 to suggest (determine, generate, predict) one or more alternative chemical compounds for a food item, where each of the alternative chemical compounds can be a substitute or replacement of a particular chemical compound that is present in the food item.

The network 102 broadly represents a combination of one or more local area networks (LANs), wide area networks (WANs), metropolitan area networks (MANs), global interconnected internetworks, such as the public internet, or a combination thereof. Each such network may use or execute stored programs that implement internetworking protocols according to standards such as the Open Systems Interconnect (OSI) multi-layer networking model, including but not limited to Transmission Control Protocol (TCP) or User Datagram Protocol (UDP), Internet Protocol (IP), Hypertext Transfer Protocol (HTTP), and so forth. All computers described herein may be configured to connect to the network 102 and the disclosure presumes that all elements of FIG. 1 are communicatively coupled via the network 102. The various elements depicted in FIG. 1 may also communicate with each other via direct communications links that are not depicted in FIG. 1 for purposes of explanation.

The server computer 106 is accessible over the network 102 by a client computer 104 to request alternative chemical compounds for a particular chemical compound that is present a food item to recreate functional properties of that particular chemical compound. The client computer 104 may comprise a desktop computer, laptop computer, tablet computer, smartphone, or any other type of computing device that allows access to the server computer 106. The elements in FIG. 1 are intended to represent one workable embodiment but are not intended to constrain or limit the number of elements that could be used in other embodiments.

3.0 Functional Overview

The server computer 106, including the compound embedding generator 108 and the compound searcher 110, and the data repository 120 interoperate programmatically in an unconventional manner to generate alternative chemical compounds for a particular chemical compound that is present a food item to recreate functional properties of that particular chemical compound.

3.1 Compound Embedding Generator

Figure 2:
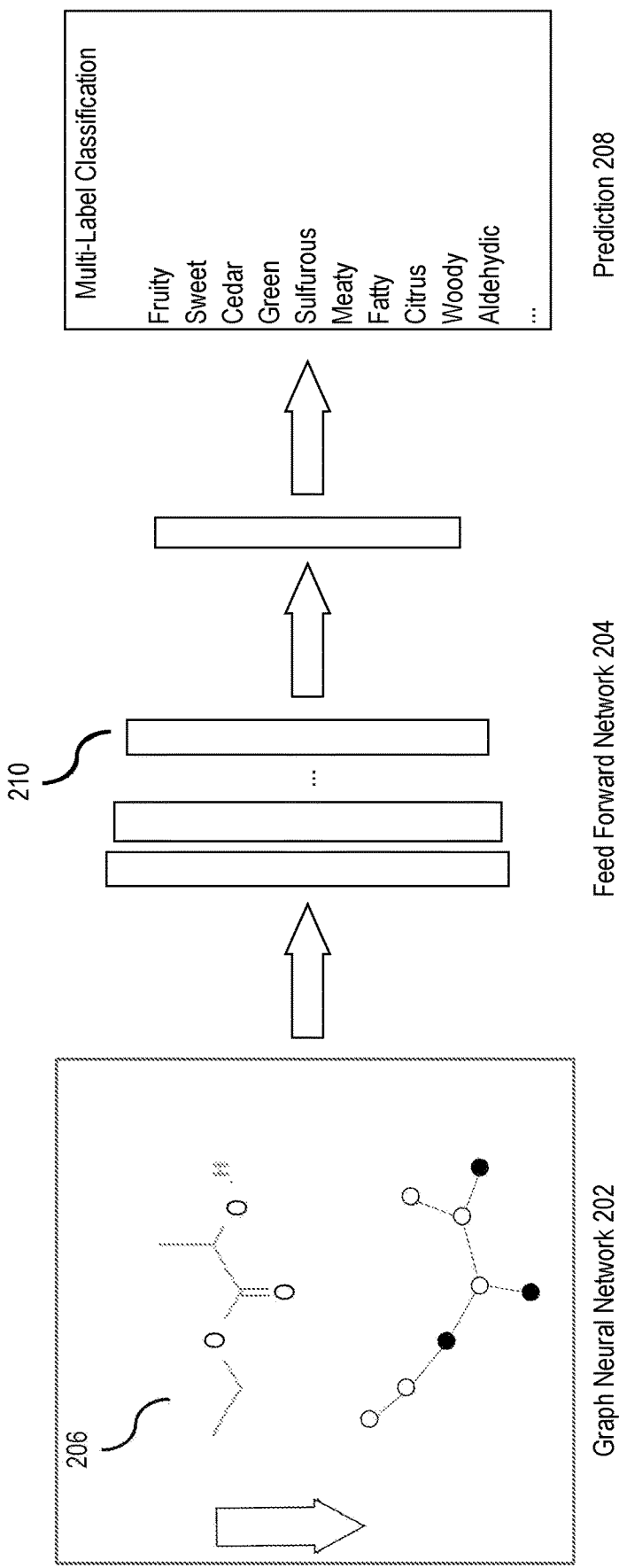
FIG. 2 illustrates an architecture of an example artificial intelligence model in accordance with some embodiments.

In an embodiment, the compound embedding generator 108 includes an artificial intelligence model that is trained to learn representations of chemical compounds (compound embeddings) in a continuous space where distances between chemical compounds can be determined. An example artificial intelligence model is a neural network based model. FIG. 2 illustrates the architecture of artificial intelligence model 200 in accordance with some embodiments. The training dataset for training the artificial intelligence model 200 includes compound structures and corresponding flavor tags and/or odor tags of at least a subset of source chemical compounds from the source compound database 124. The artificial intelligence model 200 includes two parts: a graph neural network 202 and a feed forward network 204. The feed forward network 204 includes dense layers of varying sizes. By training the artificial intelligence model 200 to predict flavors and odors, intermediate layers of the feed forward network 204 will contain information that pertains both to compound structures and associated flavors and odors.

3.1.1 Graph Neural Network

During training, a notation suitable for processing, such as the SMILES notation, of the molecular structure of each molecule (chemical compound) 206 from the training dataset is transformed into a graph. A graph is a data structure comprising nodes and edges connected together to represent information. Each node in the graph represents an atom in the molecule. Each of the nodes in the graph is initialized with a set of one or more features defining an atom, such as atomic weight, valence, and hybridization type, that corresponds with the node. The features may be obtained from an open source cheminformatics software package, such as RDKit, that contains basic information about atoms and chemical compounds. An edge between two nodes in the graph represent a bond between the atoms corresponding with the nodes.

The graph neural network 202 operates on the graph after the nodes in the graph are initialized. The graph neural network 202 performs message passing (neighborhood aggregation) between the nodes. Message passing involves pushing weights from each node to neighboring nodes that are connected via edges to that node, thus updating the internal representation for that node. Message passing is performed, in parallel, on all nodes in the graph, as information in layer L+1 depend on information in layer L. Through N iterations (e.g., N=5), the nodes know more about their own features and that of their neighboring nodes, which creates a more accurate or fuller representation of the graph (e.g., each node has more information about its neighboring nodes), where N is a hyperparameter. At the end of the message passing, each node will have a unique representation that is informed by the unique structure of the molecule.

After N iterations, a representation of the graph is an input to the feed forward network 204. A computation on all node representations is performed to obtain a vector V that represents the graph. In an embodiment, the mean of all node representations is calculated as the output of the graph neural network 202, which is input to the feed forward network 204.

3.1.2 Feed Forward Network

The feed forward network 204 includes layers of varying sizes. In the feed forward network 204, information, such as vector V associated with a source chemical compound, moves in a forward direction between the layers. During training, the feed forward network 204 uses a learning algorithm, such as gradient descent, to modify parameters (e.g., a set of weights, bias thresholds) of the feed forward network 204. The gradient descent may be based on batch gradient descent, stochastic gradient descent, or mini-batch gradient descent.

The feed forward network 204 receives vector V associated with the source chemical compound as input data and predicts flavors and odors as output data 208. In an embodiment, the feed forward network 204 is programmed to have an input layer, one or more intermediate layers, and an output layer. The size of the input data is the same as the size of the input layer. The input layer of the feed forward network is programmed to receive and pass the input data to the next layer of the feed forward network. The intermediate layers are programmed to perform intermediate processing or computation and transfer the weights from one layer to the next layer. Information generated at the last intermediate layer 210 is passed to the output layer for classification. The output layer uses a softmax function that maps the output of the intermediate layer immediately preceding it to the output data 208 of the feed forward network 204.

In an embodiment, the learning algorithm of the feed forward network 204 may be programmed as a supervised learning algorithm. As described above, the training data includes compound structures and corresponding flavor tags and/or odor tags of at least a subset of source chemical compounds from the source compound database 124. Vector V associated with the structure of a source chemical compound, as an input during training, is associated with a known target. The known target includes tagged flavors and tagged odors. The feed forward network 204 is trained by re-adjusting the set of weights and bias thresholds such that the output data of the feed forward network 204, given the input data, matches the known target. Cross-entropy or mean squared error may be used as a loss function of the feed forward network 204.

3.1.3 Compound Embeddings

After the compound embedding generator 108 is trained, the compound embedding generator 108 is applied to each of the source chemical compound in the training dataset. Since the intermediate layers of the feed forward network 204 include a distillation of structural information that are pertinent to compound flavor, compound embeddings may be retrieved or extracted from an intermediate layer of the feed forward network 204. Compound embeddings provide information regarding similarities between compound structures and compound flavors. It is noted that the closer an intermediate layer is to the output layer, the more accurate that intermediate layer is with regards to classification. In an embodiment, source compound embeddings generated by the last intermediate layer (shown in thicker lines in FIG. 2) before the output layer are retrieved. However, source compound embeddings generated by any intermediate layer may be retrieved. Source compound embeddings corresponding with the source chemical compounds in the training dataset are stored in the embedding database 126.

Similarly, the compound embedding generator 108 is applied to a particular chemical compound of a food item that is to be replaced. The particular chemical compound may be selected from a combined compound list for the food item. Compound embedding corresponding to the particular chemical compound of the food item generated by the last intermediate layer before the output layer is retrieved.

3.2 Compound Searcher

To find alternative chemical compounds that can be used to recreate the flavors of the particular chemical compound of the food item, the compound searcher 110 searches from all source compound embeddings in the embedding database 126 to find top-K chemical compounds that are most similar (closest) to compound embedding of the particular chemical compound using a distance metric. Example distance metric is cosine similarity or Euclidean similarity. Each of the top-K chemical compounds is similar to the particular chemical compound with regards to structural and functional features. This is useful if the particular compound in the food item is expensive or can only be found from an animal source.

For illustration purposes, assume a user selects ortho-gualacol, shown in Table 2, as a target chemical compound to find alternatives for. Table 3 shows top 5 alternative chemical compounds that found to be the closest to the embedding for ortho-gualacol by cosine similarity.

TABLE 2

| Compound Name | CAS No. | Formula | Kingdom | Flavor Type | Odor Type | Odor/Flavor Tags |
|---|---|---|---|---|---|---|
| Ortho-gualacol | 90-05-1 | C7 H8 O2 | Organic compounds | Woody | Phenolic | ["phenolic", "meaty", "vanilla", "spicy", . . . ] |

TABLE 3

| Compound Name | CAS No. | Formula | Kingdom | Flavor Type | Odor Type | Odor/Flavor Tags |
|---|---|---|---|---|---|---|
| Methyl salicylate | 119-36-8 | C8 H8 O3 | Organic compounds | Minty | Minty | ["aromatic", "balsamic", "caramellic", . . . ] |
| Ortho-dimethyl h . . . | 91-16-7 | C8 H10 O2 | Organic compounds | — | Vanilla | ["woody", "musty", "phenolic", "earthy", . . . ] |
| 2,6-dimethoxypl . . . | 91-10-1 | C8 H10 O3 | Organic compounds | Medicinal | Smoky | ["balsamic", "woody", "smoky", "medicinal", . . . ] |
| Ortho-anisaldehyde | 135-02-4 | C8 H8 O2 | Carbonyls, aldehydes | Anisic | Anisic | ["musty", "guaiacol", "powdery", "hawthorn", . . . ] |
| Ortho-methyl ani . . . | 578-58-5 | C8 H10 O | Phenols | Camphoreous | Naphthyl | ["wood", "warm", "nutty", "naphthyl", . . . ] |

After the alternative chemical compounds are suggested, plant-based ingredients that contain the alternative chemical compounds may be found by referencing the source compound database 124. In an embodiment, the alternative chemical compounds and/or corresponding plant-based ingredients may be returned as a result to the user.

4.0 Example Data Flow

Figure 3:
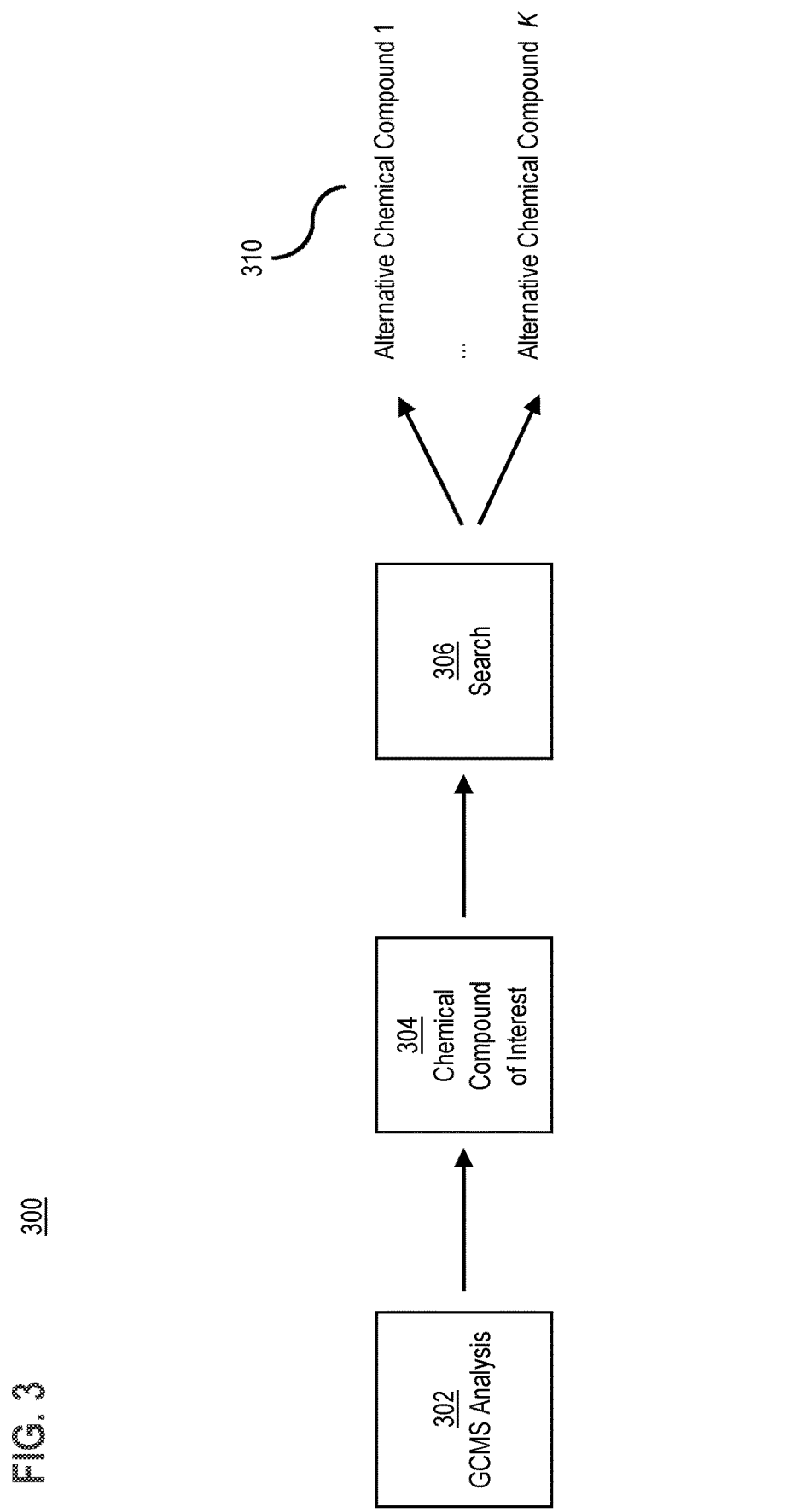
FIG. 3 illustrates an example diagram of a data flow in accordance with some embodiments.

FIG. 3 illustrates an example diagram of a data flow 300 that may represent an algorithm to form the basis of programming a computer to implement a method to find alternative chemical compounds with structural and functional properties similar to that of a particular (target) chemical compound, according to an embodiment.

GCMS techniques are used to perform GCMS analysis on food items (e.g., food items in the food item database 122)

to determine molecular compositions of these food items, at 302. A combined compound list, generated from the GCMS analysis, for each food item is stored in the food item database 122.

A particular chemical compound is identified for replacement, at 304. In an embodiment, the particular chemical compound is identified from a combined compound list of a food item that is selected from the food item database 122. The particular chemical compound is a chemical compound to be replaced. In an embodiment, the particular chemical compound is received from the client computer 104 and transmitted to the server computer 106.

A search is performed, by the server computer 106, to suggest one or more alternative chemical compounds based on the particular chemical compound of the food item that is to be replaced, at 306. Each alternative chemical compound recreates functional properties, such as flavor, smell, texture, etc., of the particular chemical compound that is present in the food item. In an embodiment, each of the source compound embeddings in the embedding database 126 is compared with the compound embedding for the particular chemical compound to find those that are closest to the compound embedding for the particular chemical compound using a distance metric, such cosine similarity.

One or more alternative chemical compounds that may be used as a replacement or substitute of the particular chemical compound are output, at 310. In an embodiment, the one or more alternative chemical components, with or without plant-based ingredients that contain the alternative chemical compounds, may be transmitted to the client computer 104 for display.

5.0 Procedural Overview

Figure 4:
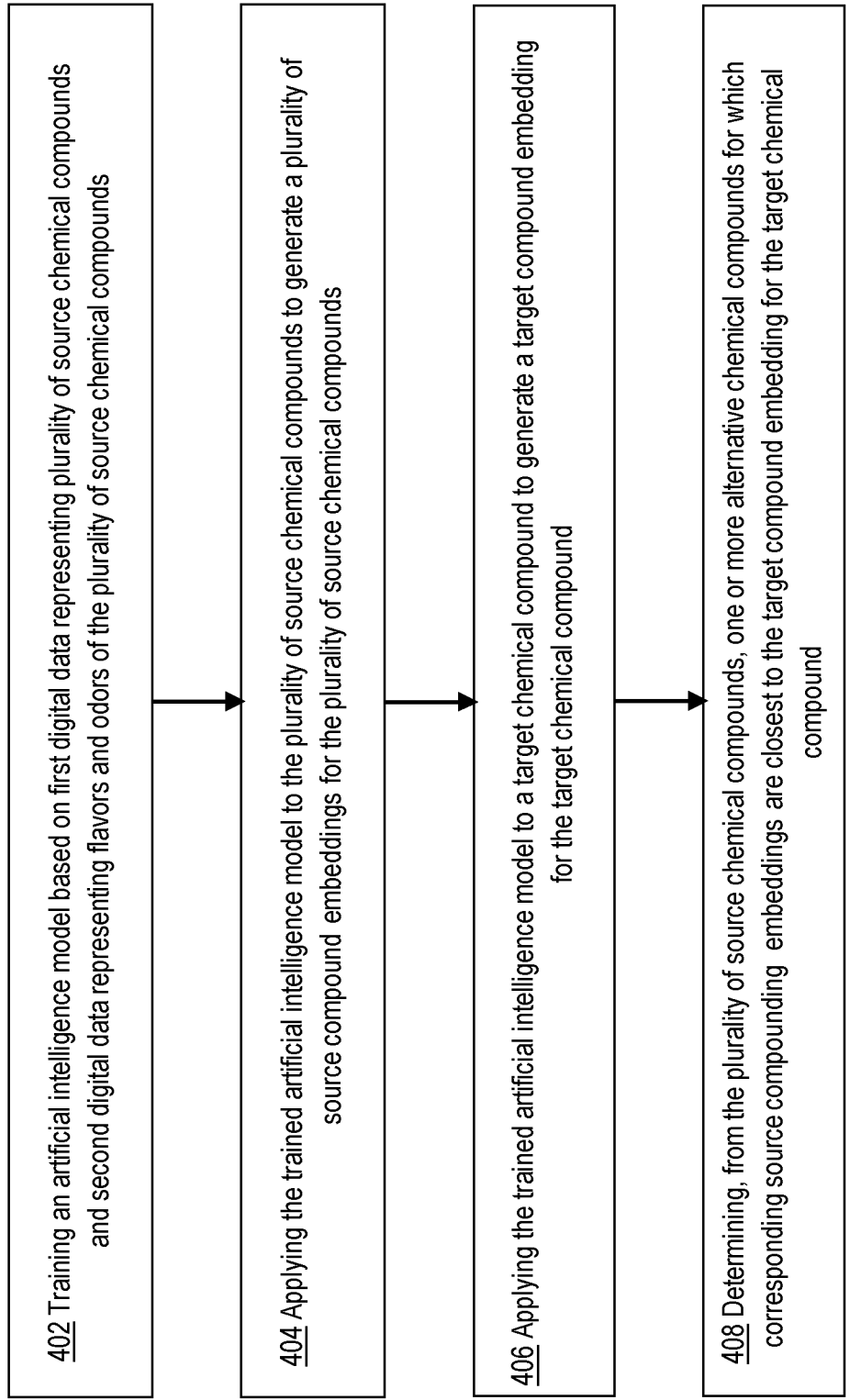
FIG. 4 illustrates an example method to suggest chemical compounds as substitutes for a chemical compound that is present in a product, in accordance with some embodiments.

FIG. 4 illustrates an example method 400 to suggest chemical compounds as substitutes for a chemical compound that is present in a food item, in accordance with some embodiments. FIG. 4 may be used as a basis to code the method 400 as one or more computer programs or other software elements that a server computer can execute or host.

At step 402, an artificial intelligence model is trained based on first digital data representing plurality of source chemical compounds and second digital data representing flavors and odors of the plurality of source chemical compounds. For example, the artificial intelligence model is the neural network based model that includes two parts: the graph neural network 202 and the feed forward network 204. The plurality of source chemical compounds is at least a subset of the source chemical compounds in the source compound database 124. The source compound database 124 includes associations between the plurality of source chemical compounds and their flavors and odors and associations between the plurality of source compounds and natural ingredients that contain them.

In an embodiment, the artificial intelligence model is trained by transforming each of the plurality of source chemical compounds into a graph that includes nodes and edges. Each node in the graph represents an atom in the molecule. Each edge in the graph represents a bond between two atoms in the molecule. Each of the nodes in the graph is initialized with a set of one or more features defining an atom, such as atomic weight, that is corresponds with the node. The features may be obtained from an open source cheminformatics software package, such as RDKit, that contains basic information about atoms and chemical compounds.

A graph neural network is applied on the graph. Multiple iterations of message passing between the nodes is performed on the graph so that the nodes understand more about their own features and that of their neighboring nodes, which creates a more accurate and fuller representation of the graph.

After the graph neural network performs multiple iterations of message passing, layers of the graph neural network are processed through dense layers of a feed forward network. In an embodiment, a representation of a graph is generated, and the representation of the graph is matched with the second digital data. For example, the representation of the graph may be generated by performing a computation on node representations of the nodes in the graph, and the representation is subsequently matched with flavors and odors of the source chemical compound associated with the graph.

At step 404, the trained artificial intelligence model is applied to the plurality of source chemical compounds to generate a plurality of source compound embeddings for the plurality of source chemical compounds. In an embodiment, the plurality of source compound embeddings is retrieved from the dense layers of the feed forward network. For example, the plurality of source compound embeddings generated or output by the second to last dense layer (e.g., by last intermediate layer) of the feed forward network may be retrieved.

At step 406, the trained artificial intelligence model is applied to a target chemical compound to generate a target compound embedding for the target chemical compound. The target chemical compound is a chemical compound that is present in a particular food item. In an embodiment, the target compound embedding is retrieved from the dense layers of the feed forward network. In an embodiment, the target compound embedding generated or output by the second to last dense layer (e.g., by last intermediate layer) of the feed forward network may be retrieved.

In an embodiment, the target chemical compound may be identified from a list of chemical compounds associated with the particular food item. The list of chemical compounds may be generated from an GCMS analysis on the particular food item. Each of the chemical compounds in the list of chemical compounds is a chemical compound that is present in the particular food item.

At step 408, one or more alternative chemical compounds for which corresponding source compounding embeddings that are closest to the target compound embedding for the target chemical compound, are determined from the plurality of source chemical compounds. Each of the one or more alternative chemical compounds determined at step 408 is a suitable chemical compound to can be used to replace the target chemical compound as it recreates functional properties of the target chemical compound. In an embodiment, the number of alternative chemical compounds determined at step 408 may be specified by a user.

In an embodiment, one or more plant-based ingredients containing the one or more alternative chemical compounds may be determined such as by referencing the source compound database 124. Each chemical compound in the source compound database 124 is associated with one or more plant-based ingredients that contain that chemical compound.

Techniques described herein speeds up research and development by suggesting alternative compounds that can be used to recreate functional properties, such as flavor, smell, texture, etc., of target compounds in food items, on which to experiment and eliminates human bias in experimentation by relying only on data for suggestions. A supervised neural network based model is trained to learn representations of compounds in a continuous space where distances between them can be determined (calculated) to suggest similar compounds.

While the techniques have been discussed with regards to compound replacement in food items, embodiments are not limited to this example. The techniques may be applied to compound replacement in fragrances, drugs, supplements, and other suitable products.

6.0 Hardware Overview

According to one embodiment, the techniques described herein are implemented by at least one computing device. The techniques may be implemented in whole or in part using a combination of at least one server computer and/or other computing devices that are coupled using a network, such as a packet data network. The computing devices may be hard-wired to perform the techniques or may include digital electronic devices such as at least one application-specific integrated circuit (ASIC) or field programmable gate array (FPGA) that is persistently programmed to perform the techniques or may include at least one general purpose hardware processor programmed to perform the techniques pursuant to program instructions in firmware, memory, other storage, or a combination. Such computing devices may also combine custom hard-wired logic, ASICs, or FPGAs with custom programming to accomplish the described techniques. The computing devices may be server computers, workstations, personal computers, portable computer systems, handheld devices, mobile computing devices, wearable devices, body mounted or implantable devices, smartphones, smart appliances, internetworking devices, autonomous or semi-autonomous devices such as robots or unmanned ground or aerial vehicles, any other electronic device that incorporates hard-wired and/or program logic to implement the described techniques, one or more virtual computing machines or instances in a data center, and/or a network of server computers and/or personal computers.

Figure 5:
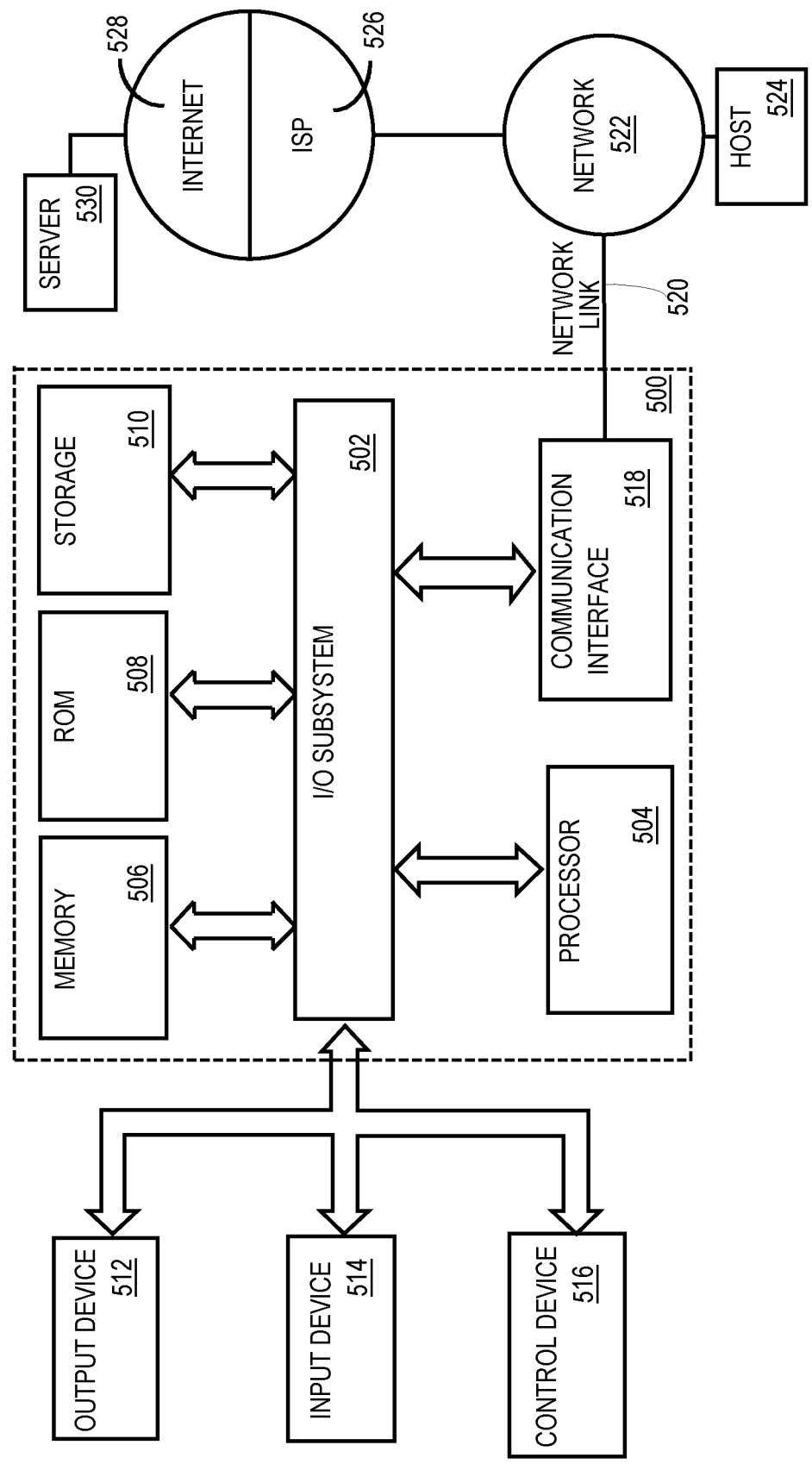
FIG. 5 illustrates a block diagram of a computing device in which the example embodiment(s) of the present invention may be embodied.

FIG. 5 is a block diagram that illustrates an example computer system with which an embodiment may be implemented. In the example of FIG. 5, a computer system 500 and instructions for implementing the disclosed technologies in hardware, software, or a combination of hardware and software, are represented schematically, for example as boxes and circles, at the same level of detail that is commonly used by persons of ordinary skill in the art to which this disclosure pertains for communicating about computer architecture and computer systems implementations.

Computer system 500 includes an input/output (I/O) subsystem 502 which may include a bus and/or other communication mechanism(s) for communicating information and/or instructions between the components of the computer system 500 over electronic signal paths. The I/O subsystem 502 may include an I/O controller, a memory controller and at least one I/O port. The electronic signal paths are represented schematically in the drawings, for example as lines, unidirectional arrows, or bidirectional arrows.

At least one hardware processor 504 is coupled to I/O subsystem 502 for processing information and instructions. Hardware processor 504 may include, for example, a general-purpose microprocessor or microcontroller and/or a special-purpose microprocessor such as an embedded system or a graphics processing unit (GPU) or a digital signal processor or ARM processor. Processor 504 may comprise an integrated arithmetic logic unit (ALU) or may be coupled to a separate ALU.

Computer system 500 includes one or more units of memory 506, such as a main memory, which is coupled to I/O subsystem 502 for electronically digitally storing data and instructions to be executed by processor 504. Memory 506 may include volatile memory such as various forms of random-access memory (RAM) or other dynamic storage device. Memory 506 also may be used for storing temporary variables or other intermediate information during execution of instructions to be executed by processor 504. Such instructions, when stored in non-transitory computer-readable storage media accessible to processor 504, can render computer system 500 into a special-purpose machine that is customized to perform the operations specified in the instructions.

Computer system 500 further includes non-volatile memory such as read only memory (ROM) 508 or other static storage device coupled to I/O subsystem 502 for storing information and instructions for processor 504. The ROM 508 may include various forms of programmable ROM (PROM) such as erasable PROM (EPROM) or electrically erasable PROM (EEPROM). A unit of persistent storage 510 may include various forms of non-volatile RAM (NVRAM), such as FLASH memory, or solid-state storage, magnetic disk, or optical disk such as CD-ROM or DVD-ROM and may be coupled to I/O subsystem 502 for storing information and instructions. Storage 510 is an example of a non-transitory computer-readable medium that may be used to store instructions and data which when executed by the processor 504 cause performing computer-implemented methods to execute the techniques herein.

The instructions in memory 506, ROM 508 or storage 510 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to parse or render files coded using HTML, XML, JPEG, MPEG or PNG; user interface instructions to render or interpret commands for a graphical user interface (GUI), command-line interface or text user interface; application software such as an office suite, internet access applications, design and manufacturing applications, graphics applications, audio applications, software engineering applications, educational applications, games or miscellaneous applications. The instructions may implement a web server, web application server or web client. The instructions may be organized as a presentation layer, application layer and data storage layer such as a relational database system using structured query language (SQL) or no SQL, an object store, a graph database, a flat file system or other data storage.

Computer system 500 may be coupled via I/O subsystem 502 to at least one output device 512. In one embodiment, output device 512 is a digital computer display. Examples of a display that may be used in various embodiments include a touch screen display or a light-emitting diode (LED) display or a liquid crystal display (LCD) or an e-paper display. Computer system 500 may include other type(s) of output devices 512, alternatively or in addition to a display device. Examples of other output devices 512 include printers, ticket printers, plotters, projectors, sound cards or video cards, speakers, buzzers or piezoelectric devices or other audible devices, lamps or LED or LCD indicators, haptic devices, actuators, or servos.

At least one input device 514 is coupled to I/O subsystem 502 for communicating signals, data, command selections or gestures to processor 504. Examples of input devices 514 include touch screens, microphones, still and video digital cameras, alphanumeric and other keys, keypads, keyboards, graphics tablets, image scanners, joysticks, clocks, switches, buttons, dials, slides, and/or various types of sensors such as force sensors, motion sensors, heat sensors, accelerometers, gyroscopes, and inertial measurement unit (IMU) sensors and/or various types of transceivers such as wireless, such as cellular or Wi-Fi, radio frequency (RF) or infrared (IR) transceivers and Global Positioning System (GPS) transceivers.

Another type of input device is a control device 516, which may perform cursor control or other automated control functions such as navigation in a graphical interface on a display screen, alternatively or in addition to input functions. Control device 516 may be a touchpad, a mouse, a trackball, or cursor direction keys for communicating direction information and command selections to processor 504 and for controlling cursor movement on display. The input device may have at least two degrees of freedom in two axes, a first axis (e.g., x) and a second axis (e.g., y), that allows the device to specify positions in a plane. Another type of input device is a wired, wireless, or optical control device such as a joystick, wand, console, steering wheel, pedal, gearshift mechanism or other type of control device. An input device 514 may include a combination of multiple different input devices, such as a video camera and a depth sensor.

In another embodiment, computer system 500 may comprise an internet of things (IoT) device in which one or more of the output device 512, input device 514, and control device 516 are omitted. Or, in such an embodiment, the input device 514 may comprise one or more cameras, motion detectors, thermometers, microphones, seismic detectors, other sensors or detectors, measurement devices or encoders and the output device 512 may comprise a special-purpose display such as a single-line LED or LCD display, one or more indicators, a display panel, a meter, a valve, a solenoid, an actuator or a servo.

When computer system 500 is a mobile computing device, input device 514 may comprise a global positioning system (GPS) receiver coupled to a GPS module that is capable of triangulating to a plurality of GPS satellites, determining and generating geo-location or position data such as latitude-longitude values for a geophysical location of the computer system 500. Output device 512 may include hardware, software, firmware and interfaces for generating position reporting packets, notifications, pulse or heartbeat signals, or other recurring data transmissions that specify a position of the computer system 500, alone or in combination with other application-specific data, directed toward host 524 or server 530.

Computer system 500 may implement the techniques described herein using customized hard-wired logic, at least one ASIC or FPGA, firmware and/or program instructions or logic which when loaded and used or executed in combination with the computer system causes or programs the computer system to operate as a special-purpose machine. According to one embodiment, the techniques herein are performed by computer system 500 in response to processor 504 executing at least one sequence of at least one instruction contained in main memory 506. Such instructions may be read into main memory 506 from another storage medium, such as storage 510. Execution of the sequences of instructions contained in main memory 506 causes processor 504 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage 510. Volatile media includes dynamic memory, such as memory 506. Common forms of storage media include, for example, a hard disk, solid state drive, flash drive, magnetic data storage medium, any optical or physical data storage medium, memory chip, or the like.

Storage media is distinct from but may be used in conjunction with transmission media. Transmission media participates in transferring information between storage media. For example, transmission media includes coaxial cables, copper wire and fiber optics, including the wires that comprise a bus of I/O subsystem 502. Transmission media can also take the form of acoustic or light waves, such as those generated during radio-wave and infra-red data communications.

Various forms of media may be involved in carrying at least one sequence of at least one instruction to processor 504 for execution. For example, the instructions may initially be carried on a magnetic disk or solid-state drive of a remote computer. The remote computer can load the instructions into its dynamic memory and send the instructions over a communication link such as a fiber optic or coaxial cable or telephone line using a modem. A modem or router local to computer system 500 can receive the data on the communication link and convert the data to a format that can be read by computer system 500. For instance, a receiver such as a radio frequency antenna or an infrared detector can receive the data carried in a wireless or optical signal and appropriate circuitry can provide the data to I/O subsystem 502 such as place the data on a bus. I/O subsystem 502 carries the data to memory 506, from which processor 504 retrieves and executes the instructions. The instructions received by memory 506 may optionally be stored on storage 510 either before or after execution by processor 504.

Computer system 500 also includes a communication interface 518 coupled to bus 502. Communication interface 518 provides a two-way data communication coupling to network link(s) 520 that are directly or indirectly connected to at least one communication networks, such as a network 522 or a public or private cloud on the Internet. For example, communication interface 518 may be an Ethernet networking interface, integrated-services digital network (ISDN) card, cable modem, satellite modem, or a modem to provide a data communication connection to a corresponding type of communications line, for example an Ethernet cable or a metal cable of any kind or a fiber-optic line or a telephone line. Network 522 broadly represents a local area network (LAN), wide-area network (WAN), campus network, internetwork, or any combination thereof. Communication interface 518 may comprise a LAN card to provide a data communication connection to a compatible LAN, or a cellular radiotelephone interface that is wired to send or receive cellular data according to cellular radiotelephone wireless networking standards, or a satellite radio interface that is wired to send or receive digital data according to satellite wireless networking standards. In any such implementation, communication interface 518 sends and receives electrical, electromagnetic, or optical signals over signal paths that carry digital data streams representing various types of information.

Network link 520 typically provides electrical, electromagnetic, or optical data communication directly or through at least one network to other data devices, using, for example, satellite, cellular, Wi-Fi, or BLUETOOTH technology. For example, network link 520 may provide a connection through a network 522 to a host computer 524.

Furthermore, network link 520 may provide a connection through network 522 or to other computing devices via internetworking devices and/or computers that are operated by an Internet Service Provider (ISP) 526. ISP 526 provides data communication services through a world-wide packet data communication network represented as internet 528. A server computer 530 may be coupled to internet 528. Server 530 broadly represents any computer, data center, virtual machine, or virtual computing instance with or without a hypervisor, or computer executing a containerized program system such as DOCKER or KUBERNETES. Server 530 may represent an electronic digital service that is implemented using more than one computer or instance and that is accessed and used by transmitting web services requests, uniform resource locator (URL) strings with parameters in HTTP payloads, API calls, app services calls, or other service calls. Computer system 500 and server 530 may form elements of a distributed computing system that includes other computers, a processing cluster, server farm or other organization of computers that cooperate to perform tasks or execute applications or services. Server 530 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to parse or render files coded using HTML, XML, JPEG, MPEG or PNG; user interface instructions to render or interpret commands for a graphical user interface (GUI), command-line interface or text user interface; application software such as an office suite, internet access applications, design and manufacturing applications, graphics applications, audio applications, software engineering applications, educational applications, games or miscellaneous applications. Server 530 may comprise a web application server that hosts a presentation layer, application layer and data storage layer such as a relational database system using structured query language (SQL) or no SQL, an object store, a graph database, a flat file system or other data storage.

Computer system 500 can send messages and receive data and instructions, including program code, through the network(s), network link 520 and communication interface 518. In the Internet example, a server 530 might transmit a requested code for an application program through Internet 528, ISP 526, local network 522 and communication interface 518. The received code may be executed by processor 504 as it is received, and/or stored in storage 510, or other non-volatile storage for later execution.

The execution of instructions as described in this section may implement a process in the form of an instance of a computer program that is being executed and consisting of program code and its current activity. Depending on the operating system (OS), a process may be made up of multiple threads of execution that execute instructions concurrently. In this context, a computer program is a passive collection of instructions, while a process may be the actual execution of those instructions. Several processes may be associated with the same program; for example, opening up several instances of the same program often means more than one process is being executed. Multitasking may be implemented to allow multiple processes to share processor 504. While each processor 504 or core of the processor executes a single task at a time, computer system 500 may be programmed to implement multitasking to allow each processor to switch between tasks that are being executed without having to wait for each task to finish. In an embodiment, switches may be performed when tasks perform input/output operations, when a task indicates that it can be switched, or on hardware interrupts. Time-sharing may be implemented to allow fast response for interactive user applications by rapidly performing context switches to provide the appearance of concurrent execution of multiple processes simultaneously. In an embodiment, for security and reliability, an operating system may prevent direct communication between independent processes, providing strictly mediated and controlled inter-process communication functionality.

7.0 Software Overview

Figure 6:
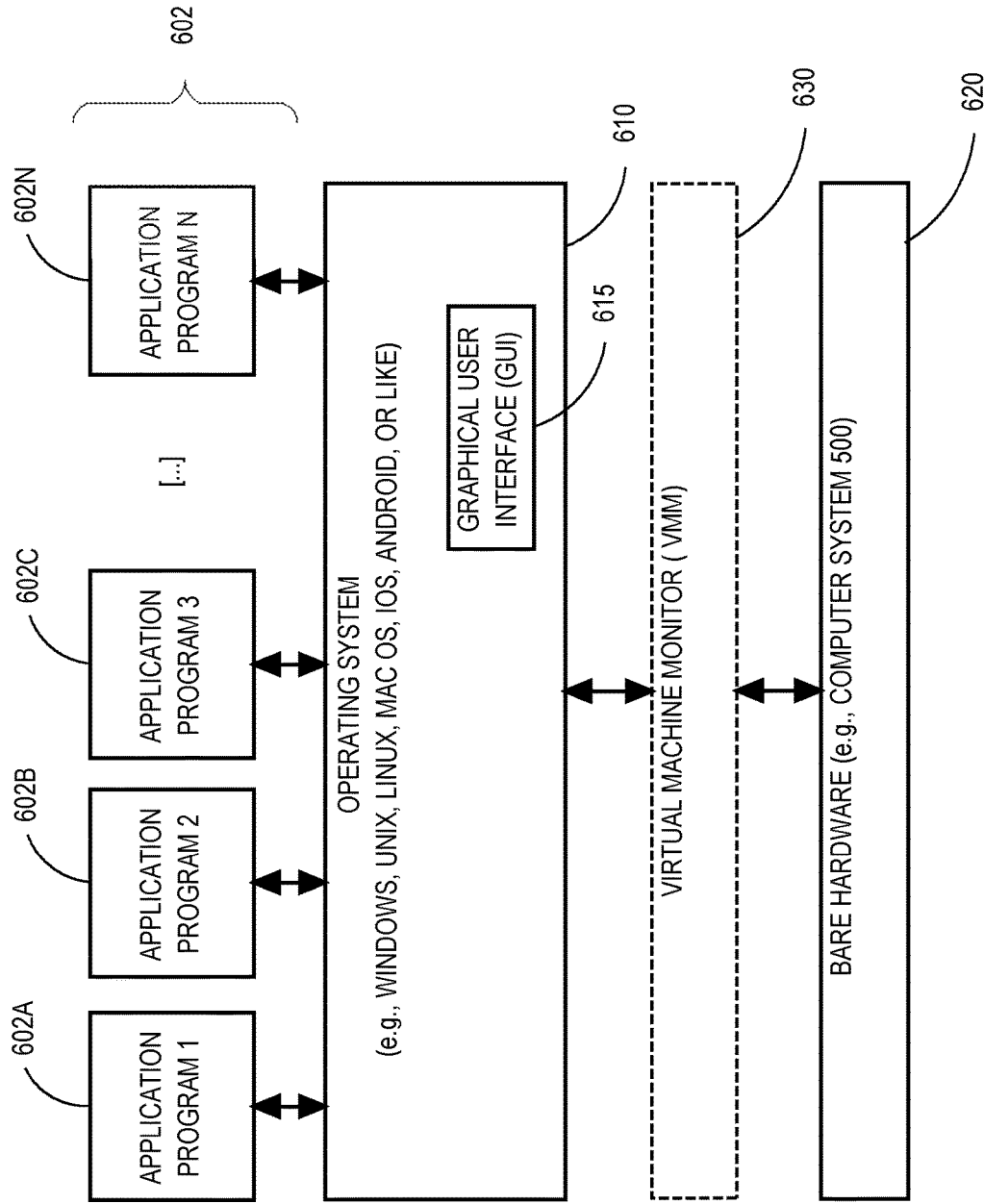
FIG. 6 illustrates a block diagram of a basic software system for controlling the operation of a computing device.

FIG. 6 is a block diagram of a basic software system 600 that may be employed for controlling the operation of computing device 500. Software system 600 and its components, including their connections, relationships, and functions, is meant to be exemplary only, and not meant to limit implementations of the example embodiment(s). Other software systems suitable for implementing the example embodiment(s) may have different components, including components with different connections, relationships, and functions.

Software system 600 is provided for directing the operation of computing device 500. Software system 600, which may be stored in system memory (RAM) 506 and on fixed storage (e.g., hard disk or flash memory) 510, includes a kernel or operating system (OS) 610.

The OS 610 manages low-level aspects of computer operation, including managing execution of processes, memory allocation, file input and output (I/O), and device I/O. One or more application programs, represented as 602A, 602B, 602C . . . 602N, may be "loaded" (e.g., transferred from fixed storage 510 into memory 506) for execution by the system 600. The applications or other software intended for use on device 600 may also be stored as a set of downloadable computer-executable instructions, for example, for downloading and installation from an Internet location (e.g., a Web server, an app store, or other online service).

Software system 600 includes a graphical user interface (GUI) 615, for receiving user commands and data in a graphical (e.g., "point-and-click" or "touch gesture") fashion. These inputs, in turn, may be acted upon by the system 600 in accordance with instructions from operating system 610 and/or application(s) 602. The GUI 615 also serves to display the results of operation from the OS 610 and application(s) 602, whereupon the user may supply additional inputs or terminate the session (e.g., log off).

OS 610 can execute directly on the bare hardware 620 (e.g., processor(s) 504) of device 500. Alternatively, a hypervisor or virtual machine monitor (VMM) 630 may be interposed between the bare hardware 620 and the OS 610. In this configuration, VMM 630 acts as a software "cushion" or virtualization layer between the OS 610 and the bare hardware 620 of the device 500.

VMM 630 instantiates and runs one or more virtual machine instances ("guest machines"). Each guest machine comprises a "guest" operating system, such as OS 610, and one or more applications, such as application(s) 602, designed to execute on the guest operating system. The VMM 630 presents the guest operating systems with a virtual operating platform and manages the execution of the guest operating systems.

In some instances, the VMM 630 may allow a guest operating system to run as if it is running on the bare hardware 620 of device 500 directly. In these instances, the same version of the guest operating system configured to execute on the bare hardware 620 directly may also execute on VMM 630 without modification or reconfiguration. In other words, VMM 630 may provide full hardware and CPU virtualization to a guest operating system in some instances.

In other instances, a guest operating system may be specially designed or configured to execute on VMM 630 for efficiency. In these instances, the guest operating system is "aware" that it executes on a virtual machine monitor. In other words, VMM 630 may provide para-virtualization to a guest operating system in some instances.

The above-described basic computer hardware and software is presented for purpose of illustrating the basic underlying computer components that may be employed for implementing the example embodiment(s). The example embodiment(s), however, are not necessarily limited to any particular computing environment or computing device configuration. Instead, the example embodiment(s) may be implemented in any type of system architecture or processing environment that one skilled in the art, in light of this disclosure, would understand as capable of supporting the features and functions of the example embodiment(s) presented herein.

8.0 Other Aspects of Disclosure

Although some of the figures described in the foregoing specification include flow diagrams with steps that are shown in an order, the steps may be performed in any order, and are not limited to the order shown in those flowcharts. Additionally, some steps may be optional, may be performed multiple times, and/or may be performed by different components. All steps, operations and functions of a flow diagram that are described herein are intended to indicate operations that are performed using programming in a special-purpose computer or general-purpose computer, in various embodiments. In other words, each flow diagram in this disclosure, in combination with the related text herein, is a guide, plan or specification of all or part of an algorithm for programming a computer to execute the functions that are described. The level of skill in the field associated with this disclosure is known to be high, and therefore the flow diagrams and related text in this disclosure have been prepared to convey information at a level of sufficiency and detail that is normally expected in the field when skilled persons communicate among themselves with respect to programs, algorithms and their implementation.

In the foregoing specification, the example embodiment(s) of the present invention have been described with reference to numerous specific details. However, the details may vary from implementation to implementation according to the requirements of the particular implement at hand. The example embodiment(s) are, accordingly, to be regarded in an illustrative rather than a restrictive sense.

What is claimed is:

1. A computer-implemented method of suggesting chemical compounds as substitutes for a chemical compound that is present in a food item, comprising:
    training an artificial intelligence model based on first digital data representing plurality of source chemical compounds and second digital data representing flavors and odors of the plurality of source chemical compounds, the first digital data including a structural representation of each source chemical compound of the plurality of source chemical compounds;
    applying the trained artificial intelligence model to the plurality of source chemical compounds to generate a plurality of source compound embeddings for the plurality of source chemical compounds, each of the plurality of source chemical embeddings includes information relating to a chemical structure and flavor of a corresponding source chemical compound, the trained artificial intelligence model is based on structures and flavors of the plurality of source chemical compounds; wherein modeling of flavors of the plurality of source chemical compounds is based on the structures of the plurality of source chemical compounds;
    applying the trained artificial intelligence model to a target chemical compound to generate a target compound embedding for the target chemical compound, the target chemical compound is a chemical compound that is present in a particular food item, the target chemical embedding includes information relating to a chemical structure and flavor of the target chemical compound; and
    determining, for each source chemical compound of the plurality of source chemical compounds, a closeness value between the target compound embedding for the target chemical compound and the source compound embedding for a respective source chemical compound, and identifying a particular source chemical compound that has the greatest closeness value among all closeness values of the plurality of source chemical compounds as an alternative chemical compound.

2. The method of claim 1, wherein training the artificial intelligence model comprises:
    transforming each of the plurality of source chemical compounds into a graph that includes nodes representing atoms of a respective source chemical compound and edges representing bonds between the atoms of the respective source chemical compound;
    applying a graph neural network on the graph;
    processing an output from layers of the graph neural network through dense layers of a feed forward network.

3. The method of claim 2, wherein processing the output from the layers of the graph neural network comprises:
    generating a representation of the graph;
    matching the representation of the graph with the second digital data.

4. The method of claim 3, wherein generating the representation of the graph comprises performing a computation on node representations of the nodes in the graph.

5. The method of claim 2, wherein the plurality of source compound embeddings for the plurality of source chemical compounds and the target compound embedding for the target chemical compound are retrieved from the dense layers of the feed forward network.

6. The method of claim 1, wherein the alternative chemical compound is determined using a distance metric.

7. The method of claim 1, further comprising:
performing gas chromatography mass spectrometry (GCMS) analysis on the particular food item;
generating, from the GCMS analysis, a list of chemical compounds, wherein each of the chemical compounds in the list of chemical compounds is a chemical compound present in the particular food item;
wherein the target chemical compound is identified from the list of chemical compounds.

8. The method of claim 1, further comprising determining one or more plant-based ingredients containing the alternative chemical compounds.

9. One or more non-transitory computer-readable storage media storing one or more instructions programmed for suggesting chemical compounds as substitutes for a chemical compound that is present in a product, when executed by one or more computing devices, cause:
training an artificial intelligence model based on first digital data representing plurality of source chemical compounds and second digital data representing functional properties of the plurality of source chemical compounds, the first digital data including a structural representation of each source chemical compound of the plurality of source chemical compounds;
applying the trained artificial intelligence model to the plurality of source chemical compounds to generate a plurality of source compound embeddings for the plurality of source chemical compounds, each of the plurality of source chemical embeddings includes information relating to a chemical structure and flavor of a corresponding source chemical compound, the trained artificial intelligence model is based on structures and flavors of the plurality of source chemical compounds; wherein modeling of flavors of the plurality of source chemical compounds is based on the structures of the plurality of source chemical compounds;
applying the trained artificial intelligence model to a target chemical compound to generate a target compound embedding for the target chemical compound, the target chemical compound is a chemical compound that is present in a particular product, the target chemical embedding includes information relating to a chemical structure and flavor of the target chemical compound; and
determining, for each source chemical compound of the plurality of source chemical compounds, a closeness value between the target compound embedding for the target chemical compound and the source compound embedding for a respective source chemical compound, and identifying a particular source chemical compound that has the greatest closeness value among all closeness values of the plurality of source chemical compounds as an alternative chemical compound.

10. The one or more non-transitory computer-readable storage media of claim 9, wherein training the artificial intelligence model comprises:
transforming each of the plurality of source chemical compounds into a graph that includes nodes representing atoms of a respective source chemical compound and edges representing bonds between the atoms of the respective source chemical compound;
applying a graph neural network on the graph;
processing an output from layers of the graph neural network through dense layers of a feed forward network.

11. The one or more non-transitory computer-readable storage media of claim 10, wherein processing the output from the layers of the graph neural network comprises:
generating a representation of the graph;
matching the representation of the graph with the second digital data.

12. The one or more non-transitory computer-readable storage media of claim 11, wherein generating the representation of the graph comprises performing a computation on node representations of the nodes in the graph.

13. The one or more non-transitory computer-readable storage media of claim 10, wherein the plurality of source compound embeddings for the plurality of source chemical compounds and the target compound embedding for the target chemical compound are retrieved from the dense layers of the feed forward network.

14. The one or more non-transitory computer-readable storage media of claim 9, wherein the alternative chemical compound is determined using a distance metric.

15. The one or more non-transitory computer-readable storage media of claim 9, wherein the one or more instructions, when executed by the one or more computing devices, further cause:
performing gas chromatography mass spectrometry (GCMS) analysis on the particular product;
generating, from the GCMS analysis, a list of chemical compounds, wherein each of the chemical compounds in the list of chemical compounds is a chemical compound present in the particular product;
wherein the target chemical compound is identified from the list of chemical compounds.

16. A computing system comprising:
one or more computer systems comprising one or more hardware processors and storage media; and
instructions stored in the storage media and which, when executed by the computing system, cause the computing system to perform:
training an artificial intelligence model based on first digital data representing plurality of source chemical compounds and second digital data representing functional properties of the plurality of source chemical compounds, the first digital data including a structural representation of each source chemical compound of the plurality of source chemical compounds;
applying the trained artificial intelligence model to the plurality of source chemical compounds to generate a plurality of source compound embeddings for the plurality of source chemical compounds, each of the plurality of source chemical embeddings includes information relating to a chemical structure and flavor of a corresponding source chemical compound, the trained artificial intelligence model is based on structures and flavors of the plurality of source chemical compounds; wherein modeling of flavors of the plurality of source chemical compounds is based on the structures of the plurality of source chemical compounds;
applying the trained artificial intelligence model to a target chemical compound to generate a target compound embedding for the target chemical compound, the target chemical compound is a chemical compound that is present in a particular product, the target chemical embedding includes information relating to a chemical structure and flavor of the target chemical compound; and determining, for each source chemical compound of the plurality of source chemical compounds, a closeness value between the target compound embedding for the target chemical compound and the source compound embedding for a respective source chemical compound, and identifying a particular source chemical compound that has the greatest closeness value among all closeness values of the plurality of source chemical compounds as an alternative chemical compound.

17. The computing system of claim 16, wherein training the artificial intelligence model comprises:

transforming each of the plurality of source chemical compounds into a graph that includes nodes representing atoms of a respective source chemical compound and edges representing bonds between the atoms of the respective source chemical compound;

applying a graph neural network on the graph;

processing an output from layers of the graph neural network through dense layers of a feed forward network.

18. The computing system of claim 17, wherein processing the output from the layers of the graph neural network comprises:

generating a representation of the graph;

matching the representation of the graph with the second digital data.

19. The computing system of claim 18, wherein generating the representation of the graph comprises performing a computation on node representations of the nodes in the graph.

20. The computing system of claim 17, wherein the plurality of source compound embeddings for the plurality of source chemical compounds and the target compound embedding for the target chemical compound are retrieved from the dense layers of the feed forward network.

* * * * *